United States Patent
Lans et al.

Patent Number: 5,888,068
Date of Patent: Mar. 30, 1999

[54] INTRACORONALLY SUPPORTED PONTIC

[75] Inventors: Maris J. Lans, Centreville, Va.; Daniel E. Purvis, Indianapolis, Ind.

[73] Assignee: Eastflex Corp., Indianapolis, Ind.

[21] Appl. No.: 855,319

[22] Filed: May 13, 1997

[51] Int. Cl.[6] .......................... A61C 13/12; A61C 13/225
[52] U.S. Cl. ............................................................. 433/181
[58] Field of Search .................................... 433/180, 181, 433/182, 183, 190, 191

[56] References Cited

U.S. PATENT DOCUMENTS

| | | | |
|---|---|---|---|
| 1,211,494 | 1/1917 | Shaw | 433/181 |
| 2,087,047 | 7/1937 | Scheven | 433/181 |
| 2,213,963 | 9/1940 | Myerson | 433/191 |
| 2,826,814 | 3/1958 | Sappey et al. | 433/181 X |
| 4,310,312 | 1/1982 | Keller et al. | 433/180 X |
| 4,445,862 | 5/1984 | Chiaramonte et al. | 433/181 X |
| 4,826,436 | 5/1989 | Shoher et al. | 433/183 X |

*Primary Examiner*—Nicholas D. Lucchesi
*Attorney, Agent, or Firm*—J. W. Gipple; Gipple & Hale

[57] ABSTRACT

The invention is directed to an intracoronally supported pontic which is uniquely anchored between two existing teeth by means of two wings which engage within slots or indentations prepared in the two existing teeth. The engaging wings are disposed on either side of a matrix around which the pontic is formed and which supports the pontic when positioned between the existing teeth. The invention further concerns the method of forming the pontic around the supporting matrix and installing it in the patient's mouth.

6 Claims, 4 Drawing Sheets

INTRACORONALLY SUPPORTED PONTIC

SUMMARY OF THE INVENTION

The present invention is directed to an intracoronally supported dental prosthesis. More particularly, the present invention teaches a means for supporting a pontic to replace a single interdental missing tooth between two adjacent natural teeth. The invention further involves a unique anchoring system for maintaining the support structure between the two adjacent teeth as well as a system for forming the pontic around the support structure.

BACKGROUND OF THE INVENTION

Problems which are uniquely associated with the prosthetic replacement of a single missing tooth, as opposed to providing an entire bridgework, have long been recognized in dental technology. One of the principle difficulties has been in providing a satisfactory support structure for the pontic so that it is maintained correctly in position between the adjacent teeth. A further problem has been providing the pontic itself and attaching it to a satisfactory support structure between adjacent teeth, particularly in view of the natural movement which occurs between opposing and adjacent teeth in the chewing process.

Systems of the prior art for providing a single pontic between adjacent teeth have involved support structures that were either (1) fixed extra coronally to the back side of adjacent teeth or (2) supported by a "Maryland bridge", which fits inside the mouth. Either of these prior art practices add bulk dimension to the adjacent teeth or inner gum area. At best it is uncomfortable and difficult to maintain in hygienic condition. It is impossible to use in cases of tight occlusions.

Accordingly, there is a need to provide a prosthetic device and procedure which can be accomplished quickly and easily in a single sitting. There is a further need for a simplified device and procedure for fixing a pontic intracoronally between adjacent teeth so as to not impinge on the inner surface of the mouth.

Besides providing a simplified procedure and device which can be implemented in a single office visit, the present invention accomplishes these objectives and additionally provides a prosthesis pontic which does not impinge on the inner surface of the mouth and which can be altered as needed to accommodate changes in tissue contours.

DESCRIPTION OF THE PRIOR ART

The following prior art is considered irrelevant to the present invention:

U.S. Pat. No. 4,917,608 to Smith describes a cranial motion dental attachment for linking the interproximal walls of adjacent molded crowns while permitting relative movement between them.

U.S. Pat. No. 4,332,563 to Weissman describes a flexible dental retaining splint which is disposable in a channel extending between adjacent teeth, the retaining splint being formed of a wire core with a wire coil being wound around the core with the turns of the coil being in a juxtaposition.

U.S. Pat. No. 4,397,634 to Biggs describes surgical pins which can be used in dental and orthopedic surgery.

U.S. Pat. No. 3,015,888 to Dent describes a pontic structure and means for maintaining the pontic within the mouth without any visible evidence thereof.

U.S. Pat. No. 2,350,196 to Saffir describes pontic blocks which comprise a plurality of pontics secured together in a form suitable for incorporation in a denture.

U.S. Pat. No. 2,022,700 to Whitely describes an anchoring pin for pontics which includes protection against deleterious effects due to oxidation and presence of acids in the oral fluids.

DETAILED DESCRIPTION OF THE INVENTION

The present invention is directed to a new intracoronally supported prosthetic replacement for single interdental missing teeth. It comprises a flat framework which can be stamped out of etched stainless steel. The framework has a central matrix portion and retention wing portions extending laterally on opposite sides of the matrix portion. Each wing portion is comprised of two parallel prongs, which provide flexion relative to axis of both prongs. The matrix portion is also doubled pronged to provide a space between the prongs for displacement of bonding compositions, such as resin.

In applying the new device, parallel slots are drilled into the interior side of each tooth adjacent to the missing tooth. These slots correspond to the two parallel prongs of the wing portion. By using a mold of the patient's dental arch, the dentist can form, shape, proportion and tint to the pontic that is specifically appropriate to the patient's specific need. This pontic superstructure is bonded to the infrastructure of the central matrix portion. The prosthetic device is then inserted from behind into the intended space, the double prongs fitting into the parallel slots in the adjacent teeth. When in place, the double pronged wings are bonded, sealed and covered with resin or other bonding composition, so that the interior surface of the adjacent tooth is as it was before installation. Methacrylate acrylate can be used to attach cosmetic gold pontics to the support structure of the invention. The invention makes it possible to install the pontic during a single visit to the dentist; and the design of the invention is meant to receive all current dental restorative materials as the pontic superstructure. The invention can be fitted with silver alloy, hammered gold or hybird etched precious metal surfaces as well as resins for its pontic superstructure.

The double prong retention wings of the invention allow for flexion about two axis. This allows one prong of each wing to be in compression while the other is in tension and provides translation forces that reduce the disruptive forces at the tooth-resin interface. The double prongs of the matrix portion provides a space between the prongs for uniform resin displacement when the pontic is bonded to the matrix portion. This limits major voids formed at the bonded interfaces.

The invention will however be more fully appreciated by having specific reference to the drawings which illustrate a preferred embodiment thereof.

Figure 1:
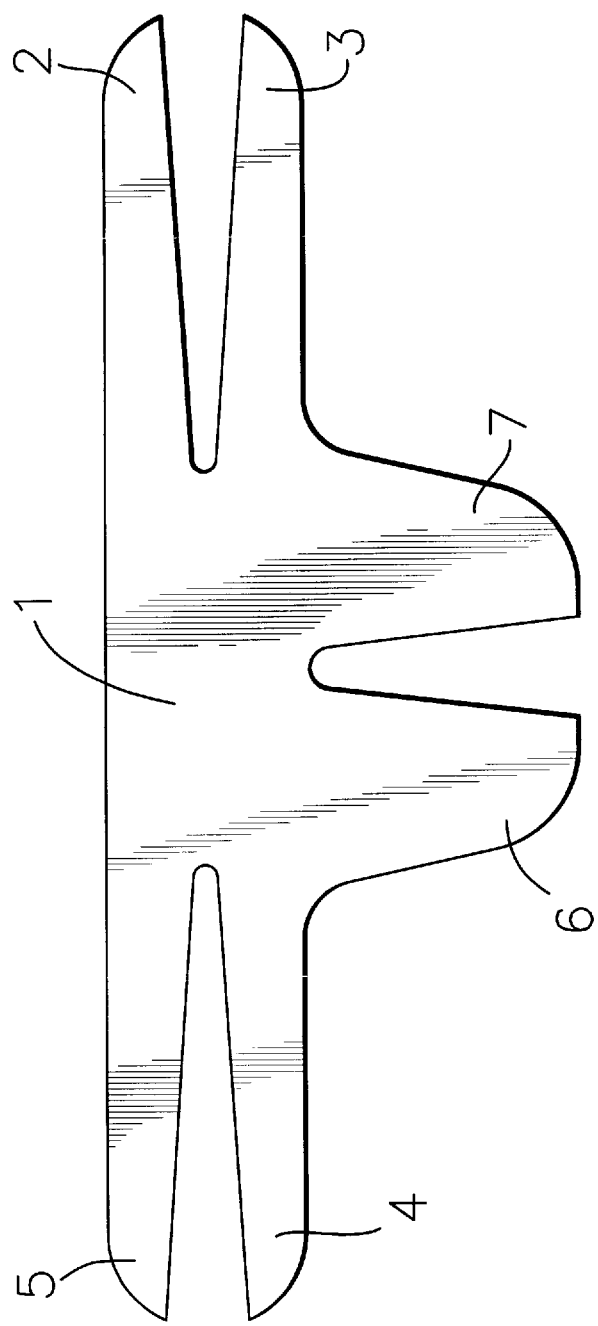
FIG. 1 illustrates the pontic support structure of the invention.

Directing attention to FIG. 1 of the drawings, the support structure employed for replacement of a missing tooth is shown consisting of a matrix portion 1 having two opposing engagement members each of which comprises a pair of parallel prongs 2, 3, 4 and 5 which are adapted to fit within parallel slots drilled in the two teeth adjacent the missing tooth. The matrix portion 1 is provided with two spaced apart parallel extensions 6 and 7 which are transverse to the opposed parallel prongs.

Figure 2:
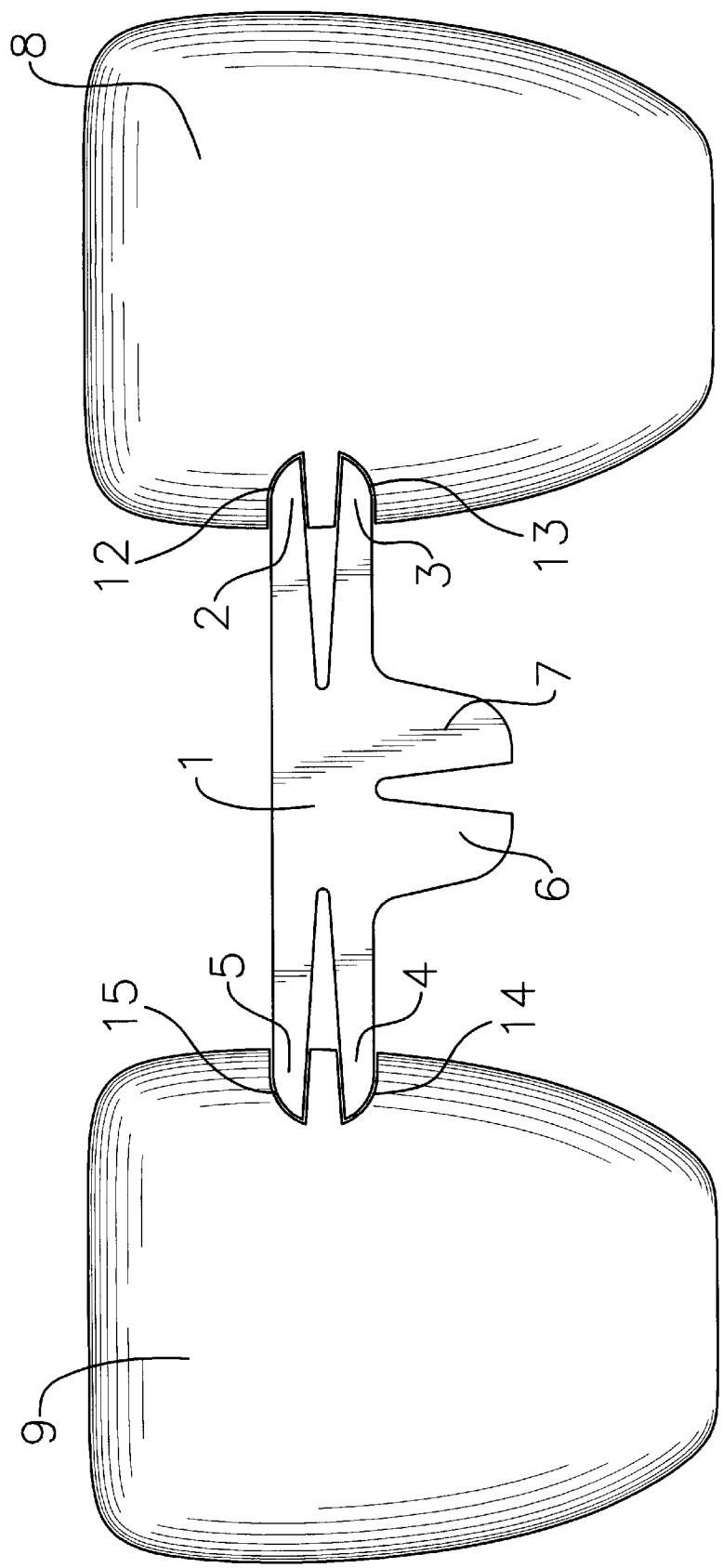
FIG. 2 illustrates the adjacent teeth provided with slots to accommodate the pontic support structure of the invention.

As illustrated in FIG. 2 of the drawings, parallel slots 12, 13, 14 and 15 are drilled in adjacent teeth 8 and 9 to accommodate the respective opposing engagement members comprising parallel prongs 2, 3, 4 and 5.

Figure 3:
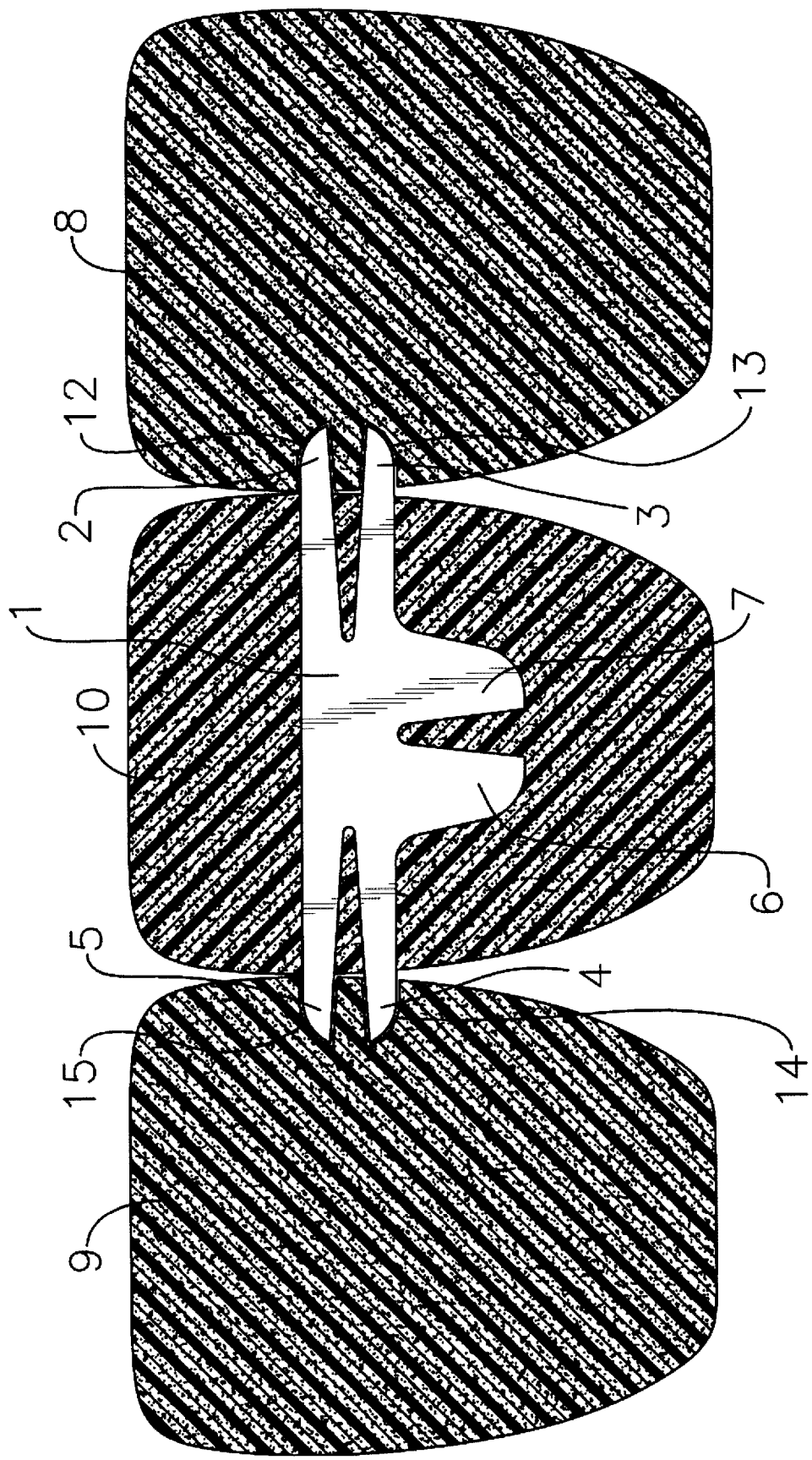
FIG. 3 is a front plan cut-away view illustrating the entire dental prosthesis including the support structure and pontic in place between two adjacent teeth in accordance with the invention.

FIG. 3 of the drawings illustrates implacement of the pontic 10 between two natural teeth 8 and 9. As shown, the opposed parallel prongs 2, 3, 4 and 5 are respectively engaged within the parallel slots 12, 13, 14 & 15 provided in the teeth 8 and 9 disposed on either side of the gap formed by the missing tooth.

Figure 4:
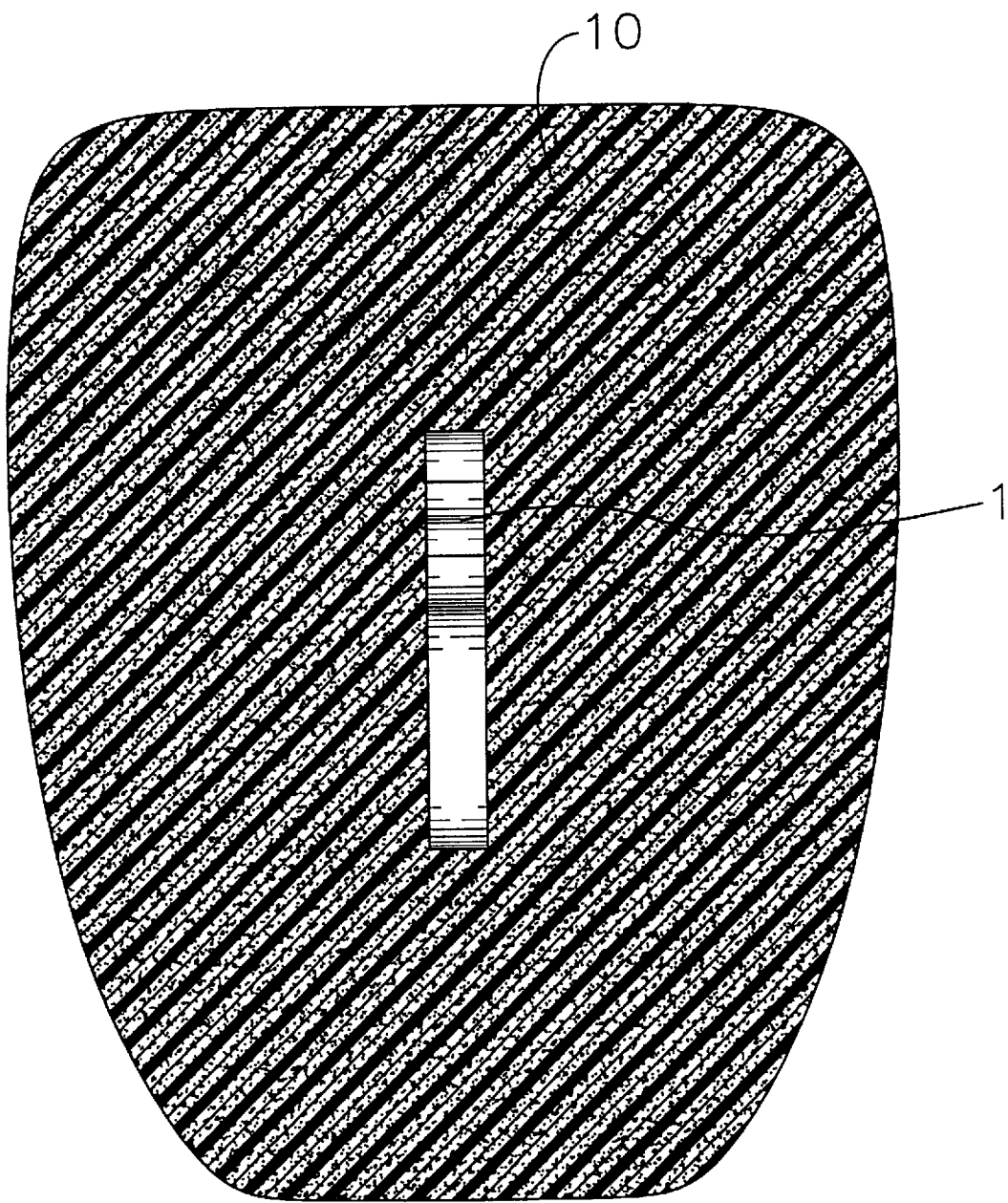
FIG. 4 is a side plan cut away view illustrating the pontic formed on the support structure of the invention.

In FIG. 4, the matrix portion 1 is seen embedded within the superstructure 10 forming the pontic.

The intracoronally supported dental prosthesis of the present invention provides several advantages in addition to those described above, particularly with respect to pediatric and geriatric dentistry. In pediatric dentistry there is often a need for space management in the primary and secondary dentition. The present invention without modification can be used to fabricate fixed spaced maintenance appliances. Due to the refractive sizing, the invention can also be used in the fabrication of space regaining appliances. The advantage of the present invention over existing prior art in pediatric applications is that in the majority of prior art appliances the missing tooth space is first filled by a removable acrylic appliance which can be easily lost and which requires that the adjacent teeth be stripped to accommodate bands which are often necessary to retain the appliance. Because there is no visible metallic component in the present invention, aesthetics are far more acceptable to children as well as parents. Further, the present invention requires only that the support structure be suspended between the adjacent teeth and therefore does not bear down on the gingival tissue. Prior art devices in which pressure is exerted against gingival tissues can be uncomfortable for the patient in cases where an expected tooth is erupting beneath. Further, the cost of replacing a lost or removable retainer can increase the overall cost of orthodontic treatment. In children with handicaps from gross physical motor deficiencies to mild speech impediments, the fixed nature of the present invention is an obvious improvement over any removable appliance. Because the pontic can be easily modified and/or repaired, changes in gingival contour can be accommodated without extensive procedures. Identification chips can be placed inside the prosthesis of the invention to aid in the identification of lost children or for forensic investigations.

With regard to geriatric applications, conventional crowns and bridges usually require several appointments with the dentist, multiple local anesthetic injections and reduction of the enamel surface of the teeth and disruption of the pericoronal gingival attachment. The stresses of these procedures are often contra-indicated for the geriatric or medically compromised population. A shorter procedural time with the dentist lowers the cost of the procedure. The present invention can also be utilized as a periodontal splinting appliance to help stabilize the supporting teeth without excessive torque that would be unavoidable with a removable or conventionally fixed pontic and can be used in conjunction with the periodontal splint.

Because of the atrophy of the pulp chamber and formation of secondary dentin in older patients, the need for local anesthesia is often unnecessary in accordance with the procedure of the present invention as it requires only very conservative preparations. Fluoride releasing composites can be utilized to minimize the reduction of carries. This is an option that is not available with conventional procedures and appliances. Children can also benefit from the fluoride releasing composites. The procedure allows for the improvement of the contact point between the pontic and the adjacent supporting teeth by the ability to bond to the supporting teeth in a dynamic manner. This is achieved by bonding the teeth during occlusal loading. Conventional bridges are cast or fabricated for a passive fit. Supporting teeth cannot move during the prior art occlusal loading regardless of how heavy the cementation force is. The attachment system of the invention allows the pontic and support structure to move in relation to the occlusal load because the resin is not completely set until it is cured. The procedure for bonding the support structure allows the dentist to fine tune the position of the pontic during the actual placement, which is something that conventional bridgework does not allow. Unique to the present invention is the occlusal loading during bonding, placing the root surface of the supporting tooth on the pontic side in tension. Tension promotes osteoblastic activity which in turn promotes bone growth as opposed to conventional bridges which reduce the amount of bone because of gingival destruction. The present invention is therefore a constructive procedure because it improves interproximal contact, and promotes bone growth during its service in the patient's mouth, whereas the convention bridge is destructive to the contacts and supporting bone, and gingival margins.

Further because of the osteoblastic activity associated with the present invention, an implant placed underneath it will be more rapidly and completely osteo-integrated thereby reducing the healing time significantly. Because the present invention is suspended over the implant site, there is no unfavorable pressure being directly exerted upon the pontic and the freshly healing gingival tissues, thereby greatly adding to patient comfort and the improved healing of the site of the surgery.

It should be noted that in performing the process of this invention, the pontic can be formed in situ around the support structure that is already intracoronally affixed to the adjacent teeth, or alternatively the pontic can be formed out of the mouth around the support structure, and the entire prosthetic device then installed between two adjacent teeth as described above. In the latter process, which is the one preferred in most circumstances, a mold is made of the dental arch including the gap formed by the missing tooth. Working with the mold, a pontic which is perfectly calculated for the gap can be formed in the laboratory using the latest and best techniques and materials with the support structure imbedded therein. When it is completed, it is then installed in the patient's mouth which does not take much of the patient's or dentist's time. The process requires two visits to the dentist (i.e. (1) to cast the mold (2) to install the prosthetic device). However, in some circumstances where it may be necessary to have an immediate replacement of a mising tooth, the pontic can be formed in situ on the installed support structure all in one sitting. It will of course be appreciated that the cast pontic can then be finally configured by typical grinding techniques both to facilitate its bite and interaction with other teeth and its appearance.

Other modifications and alternatives to the herein described procedures and components will be apparent to those of ordinary skill this art and are considered to fall within the scope of the claims defining this invention.

What is claimed is:

1. A dental prosthesis support structure for receiving and supporting a pontic and attaching it intracoronally between a pair of existing teeth, said support structure comprising a matrix for supporting said pontic and two opposed wings each extending laterally on either side of said matrix for engagement within corresponding slots formed in the said pair of existing teeth, said support structure being a flat framework of stainless steel.

2. The dental structure of claim 1 wherein each of said opposed wings comprises a pair of parallel prongs which extend away from said pontic to engage within said slots.

3. The dental structure of claim 1 wherein said matrix is provided with an extension for anchoring it within said pontic.

4. The dental structure of claim 3 wherein said extension comprises two parallel prongs aligned transverse to said opposed wings.

5. A method for attaching and supporting a pontic intracoronally in a gap between a pair of existing teeth which comprises:

forming an impression of the dental arch within said gap and forming slots in said existing teeth adjacent gap to receive respective engagement extensions of a support structure for said pontic;

forming said pontic in said impression around a matrix having attached thereto on either side said engagement extensions to form said pontic support structure wherein each of said engagement extensions comprises a pair of spaced parallel prongs and said matrix comprises a pair of parallel prongs aligned transverse to said engagement extensions;

engaging and adhering said engagement extensions within said slots to thereby anchor said pontic intracoronally between said pair of existing teeth.

6. A method for attaching and supporting a pontic intracoronally in a gap between a pair of existing teeth which comprises:

anchoring a support structure for said pontic between said pair of existing teeth by forming slots in said existing teeth adjacent said gap to receive respective engagement extensions on a matrix forming said support structure and engaging and adhering said engagement extensions within said slots to thereby anchor said support structure intracoronally between said pair of existing teeth, wherein each of said engagement extensions comprise a pair of spaced parallel prongs and said matrix comprises a pair of parallel prongs aligned transverse to said engagement extensions;

forming the pontic in situ from dental material between said existing teeth and around said matrix so that it is disposed and anchored in said gap.

* * * * *